US007851653B2

(12) United States Patent
Getman et al.

(10) Patent No.: US 7,851,653 B2
(45) Date of Patent: Dec. 14, 2010

(54) METHOD OF CREATING A SOLVENT-FREE POLYMERIC SILICON-CONTAINING QUATERNARY AMMONIUM ANTIMICROBIAL AGENT HAVING SUPERIOR SUSTAINED ANTIMICROBIAL PROPERTIES

(75) Inventors: Gerry D. Getman, McMurray, PA (US); Matt Bootman, Cannonsburg, PA (US); Donald Wagner, Jr., Bridgeville, PA (US); Thomas Ward, Hudson, FL (US)

(73) Assignee: Biosafe, Inc., Pittsburgh, PA (US)

( * ) Notice: Subject to any disclaimer, the term of this patent is extended or adjusted under 35 U.S.C. 154(b) by 444 days.

(21) Appl. No.: 11/386,485

(22) Filed: Mar. 22, 2006

(65) Prior Publication Data

US 2006/0223962 A1  Oct. 5, 2006

Related U.S. Application Data

(60) Provisional application No. 60/664,222, filed on Mar. 22, 2005, provisional application No. 60/702,201, filed on Jul. 25, 2005.

(51) Int. Cl.
C07C 211/00 (2006.01)

(52) U.S. Cl. .................................. 564/295; 427/384

(58) Field of Classification Search ................. 427/384; 564/295
See application file for complete search history.

(56) References Cited

U.S. PATENT DOCUMENTS

| | | | |
|---|---|---|---|
| 3,560,385 A | 2/1971 | Roth | |
| 3,695,921 A | 10/1972 | Shepherd | |
| 3,730,701 A | 5/1973 | Isquith | |
| 3,794,736 A | 2/1974 | Abbott | |
| 3,814,739 A | 6/1974 | Takeda | |
| 3,860,709 A | 1/1975 | Abbott | |
| 3,888,728 A | 6/1975 | Petrik et al. | |
| 4,255,480 A | 3/1981 | Scher et al. | |
| 4,282,366 A | 8/1981 | Eudy | |
| 4,394,378 A | 7/1983 | Klein | |
| 4,408,996 A | 10/1983 | Baldwin | |
| 4,411,928 A | 10/1983 | Baldwin | |
| 4,414,268 A | 11/1983 | Baldwin | |
| 4,504,541 A | 3/1985 | Yasuda | |
| 4,605,564 A | 8/1986 | Kulla | |
| 4,614,675 A | 9/1986 | Ona | |
| 4,615,937 A | 10/1986 | Bouchette | |
| 4,620,878 A | 11/1986 | Gee | |
| 4,631,273 A | 12/1986 | Blehm | |
| 4,675,347 A | 6/1987 | Mochizuki | |
| 4,692,374 A | 9/1987 | Bouchette | |
| 4,842,766 A | 6/1989 | Blehm | |
| 4,847,088 A | 7/1989 | Blank | |
| 4,865,870 A | 9/1989 | Hu | |
| 4,999,210 A | 3/1991 | Solomon | |
| 5,024,875 A | 6/1991 | Hill | |
| 5,053,048 A | 10/1991 | Pinchuk | |
| 5,064,613 A | 11/1991 | Higgs | |
| 5,069,899 A | 12/1991 | Whitbourne | |
| 5,290,894 A | 3/1994 | Melrose | |
| 5,340,583 A | 8/1994 | Dziabo et al. | |
| 5,358,688 A | 10/1994 | Robertson | |
| 5,359,104 A | 10/1994 | Higgs | |
| 5,399,737 A | 3/1995 | Park et al. | |
| 5,411,585 A | 5/1995 | Avery | |
| 5,536,861 A | 7/1996 | Robertson | |
| 5,624,704 A | 4/1997 | Darouiche | |
| 5,753,733 A | 5/1998 | Eck | |
| 5,954,869 A | 9/1999 | Elfersy | |
| 5,959,014 A | 9/1999 | Liebeskind | |
| 6,113,815 A | 9/2000 | Elfersy | |
| 6,120,587 A | 9/2000 | Elfersy | |
| 6,146,688 A | 11/2000 | Morgan | |
| 6,221,944 B1 | 4/2001 | Liebeskind | |
| 6,329,490 B1 * | 12/2001 | Yamashita et al. | 528/42 |
| 6,376,696 B1 | 4/2002 | Raab | |
| 6,469,120 B1 | 10/2002 | Elfersy | |

(Continued)

FOREIGN PATENT DOCUMENTS

| | | | |
|---|---|---|---|
| EP | 0090577 | * | 10/1983 |
| EP | 0351957 A2 | | 1/1990 |
| EP | 0 415 540 B1 | | 7/1990 |
| WO | WO 94/13748 A1 | | 6/1994 |
| WO | WO 97/42200 A1 | | 11/1997 |
| WO | WO 00/54587 A1 | | 9/2000 |

OTHER PUBLICATIONS

Sauvet et al. "Biocidal Polymers Active by Contact. V. Synthesis of Polysiloxanes with Biocidal Activity" J. Appl. Polym. Sci. vol. 75, 2000, pp. 1005-1012.*

Merker et al., "The Reaction of Alkyl Halides with Carboxylic Acids and Phenols in the Presence of Tertiary Amines", The Journal of Organic Chemistry, vol. 26, pp. 581 and 582 (1961).

(Continued)

Primary Examiner—Michael Barr
Assistant Examiner—Robert S Walters, Jr.
(74) Attorney, Agent, or Firm—Panitch Schwarze Belisario & Nadel LLP

(57) ABSTRACT

An antimicrobial polymer is disclosed containing silicon-containing quaternary ammonium groups, the polymer including in its structure repeating units of Formula II:

$$R_3N^+R^0{}_n SiX'_{4-n} Y^- \quad (II)$$

wherein each R and each $R^0$ is independently a non-hydrolysable organic group; each X' is —OR', —OH or —O—Si, wherein R' is an alkyl group of 1 to about 22 carbon atoms, or an aryl group of 6 carbon atoms; n is an integer of 0 to 3; and Y is an anionic moiety suitable to form the salt of the repeating units of Formula II. Also disclosed are methods of making such a polymer and imparting sustained antimicrobial properties to a substrate using the polymer.

56 Claims, No Drawings

U.S. PATENT DOCUMENTS

| | | | |
|---|---|---|---|
| 6,572,926 B1 | 6/2003 | Morgan | |
| 6,613,755 B2 * | 9/2003 | Peterson et al. | 514/63 |
| 6,632,805 B1 | 10/2003 | Liebeskind | |
| 6,762,172 B1 | 7/2004 | Elfersy | |
| 6,790,910 B1 * | 9/2004 | Sosna et al. | 525/191 |
| 2003/0096934 A1 * | 5/2003 | Jost et al. | 528/10 |

OTHER PUBLICATIONS

"The Handling and Use of AEGIS Microbe Shield™ Technology," Form 7E4, AEGIS Environments, Midland, MI USA Rev. Oct. 2004, pp. 1-12.

Office Action dated May 12, 2009 in corresponding U.S. Appl. No. 11/386,348, 11 pages.

* cited by examiner

METHOD OF CREATING A SOLVENT-FREE POLYMERIC SILICON-CONTAINING QUATERNARY AMMONIUM ANTIMICROBIAL AGENT HAVING SUPERIOR SUSTAINED ANTIMICROBIAL PROPERTIES

CROSS-REFERENCE TO RELATED APPLICATIONS

This application claims the benefit of U.S. Provisional Patent Application No. 60/664,222, filed Mar. 22, 2005, and U.S. Provisional Patent Application No. 60/702,201, filed Jul. 25, 2005, the disclosures of which are hereby incorporated herein by reference in their entireties.

BACKGROUND OF THE INVENTION

This invention relates to a novel silicon-containing antimicrobial polymer composition and to a method of creating a solvent-free formulation of such polymeric antimicrobial material, preferably in the form of a dry powder or in solution in a solvent in order to impart antimicrobial activity unto or in another material. The antimicrobial polymer has superior antimicrobial properties compared to the similar monomer.

More particularly, this invention relates to a novel way to form an antimicrobial material that can be incorporated in or bound to a substrate such that it has a non-leaching antimicrobial property that is not dependent on the mechanism of leaching antimicrobial agents. The method described herein may be used to prepare or treat biocompatible devices or other products and impart antimicrobial properties to substrates containing the antimicrobial agent throughout the polymeric substrates. Additionally, the method described herein may be used to prepare or treat biocompatible devices or other products and impart antimicrobial properties to polymeric substrates containing the antimicrobial agent bound to the surface of the polymeric substrates. Further, the method described herein may be used to prepare liquid solutions with antimicrobial properties.

There has been a great deal of attention in recent years given to the hazards of bacterial contamination from potential everyday exposure. Noteworthy examples of such concerns include the fatal consequences of food poisoning due to certain strains of *Eschericia coli* being found within undercooked beef in fast food restaurants; *Salmonella* contamination causing sicknesses from undercooked and unwashed poultry food products; and illnesses and skin infections attributed to *Staphylococcus aureus, Klebsiella pneumoniae*, yeast, and other unicellular organisms. With such an increased consumer interest in this area, manufacturers have begun introducing antimicrobial agents within various everyday products and articles. For instance, certain brands of polypropylene cutting boards, liquid soaps, etc., all contain antimicrobial compounds.

Silicon-containing quaternary ammonium antimicrobial agents belong to a general class of antimicrobial agents termed cationic antimicrobial agents. This invention relates to a solvent-free polymer composition and to a method of creating a polymeric silicon-containing quaternary ammonium antimicrobial agent that is more effective than the monomeric form in solutions. As used herein, an "antimicrobial agent" is an agent that destroys or inhibits the growth of microorganisms, and particularly pathogenic microorganisms. The major classes of microorganisms are bacteria, fungi including mold and mildew, yeasts, and algae. Microorganisms can be found in the air, the water, in and on the human body and bodies of animals, soil, wastes, and on all surfaces. The microorganisms are deposited from the air, food and drink spills, dust, and dirt and tracked in soil, and from human and animal excreta such as sweat, urine, and feces. Organisms grow and multiply when there is available a nutrient source of food such as organic or inorganic material contained in such wastes, dirt, dust, and living tissue. For growth and multiplication, most microorganisms also require warm temperatures, and moisture. When these conditions exist, microorganisms multiply, grow and flourish. Microbial growth, however, leads to many problems, such as unpleasant odors ranging from stale to musty and mildew-like, to putrid and foul smelling, resembling ammonia. The growths also produce unsightly stains, discoloration, and deterioration of many surfaces and materials in which they come into contact. A more serious disadvantage of microbial growth is the proliferation of pathogenic microorganisms, their metabolic products and their somatic and reproductive cell parts, which contribute to the spread of disease, infection, and health disorders.

Silicon-containing quaternary ammonium salts having the following Formula I are recognized antimicrobial agents:

$$R_3N^+R^o{}_nSiX_{4-n}Y^- \quad (I)$$

Wherein each R and each $R^o$ is independently, a non-hydrolysable organic group; each X is, independently, a hydrolysable group; n is an integer of 0 to 3; and Y is a suitable anionic moiety to form the salt of the compound of Formula I. Such silicon containing quaternary ammonium antimicrobial agents are typically manufactured and supplied in solvents such as methanol.

The use of such silicon-containing quaternary ammonium salts in solvents adsorbed by a polymeric substrate where the quaternary salt is subsequently polymerized such that an interpenetrating network is formed within the interstices only of the polymeric substrate surface has been described in U.S. Pat. Nos. 6,146,688 and 6,572,926, the disclosures of which are hereby incorporated herein by reference. The referenced patents teach the use of the monomeric antimicrobial agents to form the interpenetrating networks in the surface pores, but make no claims as to the use of the polymeric form of the antimicrobial agents.

Despite knowledge of the common usage of silicon-containing quaternary ammonium salt monomers for imparting antimicrobial properties to solid surfaces, a method was not known for protecting surfaces through the use of polymerized silicon-containing quaternary ammonium salt polymers incorporated throughout the entire substrate or bound to the surface of the substrate. This is accomplished with the present invention.

The use of such silicon-containing quaternary ammonium compounds as antimicrobial agents in accordance with the prior art is well known and taught in a wide variety of U.S. Pat. Nos. e.g., 3,560,385; 3,794,736; 3,814,739; 5,954,869; the disclosures of which are hereby incorporated herein by reference. It is also taught that these compounds possess certain antimicrobial properties, which make them valuable and very useful for a variety of surfaces, substrates, instruments and applications (see, e.g., U.S. Pat. Nos. 3,730,701; 3,794,736; 3,860,709; 4,282,366; 4,394,378; 4,408,996; 4,414,268; 4,504,541; 4,615,937; 4,620,878; 4,631,273; 4,692,374; 4,842,766; 5,064,613; 5,358,688; 5,359,104; 5,411,585; 5,954,869; 5,959,014; 6,113,815; 6,120,587; 6,221,944; 6,469,120; 6,632,805; and 6,762,172; the disclosures of which are hereby incorporated herein by reference).

These silicon-containing quaternary ammonium antimicrobial compounds are available and widely used as disinfectants and biocides and to treat items that may undesirably support microbial growth. For example, methanol-containing, silicon-containing quaternary ammonium salts are used to treat carpeting, walls, various commercial products such as sponges and fabrics, and even water. They are also used to rehabilitate "sick buildings," particularly after floods and water leaks, and reduce odors caused by mildew, fungi and bacterial growth in damp basement areas.

Most commercially available silicon-containing quaternary ammonium salts are generally pre-packaged in water or alcohol solutions of approximately 2 weight % to approximately 3 weight %, or less, quaternary salt concentration. They are applied to substrates, such as carpets, walls and floors, to kill the bacteria. The silicon-containing quaternary ammonium salt is often applied in a fine spray. When treating fabrics, sponges, bedding, and similar products, the concentration of the quaternary ammonium salt generally can be much lower, e.g., less than 1 weight %.

More specifically, because hospital-acquired infections are the leading cause of hospital or long-term care infections, numerous attempts have been made to create antimicrobial surfaces in hospital and medical facilities. Most treatments rely on the use of antimicrobial washes to achieve a coated surface that is resistant to bacterial growth. Unfortunately, this indiscriminate use of antimicrobial agents results in the build up of increased resistance of bacteria and certain other microorganisms to the widely used antimicrobial agents. This presents a significant problem for those being treated in health care facilities, and particularly for immune-compromised patients.

Further, some antimicrobial surface treatments use a coating treatment that provides a vehicle for entrapping the antimicrobial agent on the surface but permits subsequent diffusion of the antimicrobial agent into the biological environment. Many such treatments rely upon a leaching mechanism to deliver the antimicrobial agent into the environment.

Thus, a method has not been devised to impart to a substrate a non-leaching, biocompatible, chemically bonded antimicrobial properties throughout the entire substrate. Only the very surface has previously been made antimicrobial with a non-leaching antimicrobial agent through the formation of an interpenetrating network at the interface of the substrate surface and the antimicrobial agent, for only as deep into the surface as the antimicrobial agent could be adsorbed into the substrate. The present invention of chemically bonding or physically mixing a silicon-containing quaternary ammonium salt of Formula II (below) and a polymeric substrate, preferably in the form of a bulk resin substrate so made and methods of using such bulk resin accomplishes this goal. Thus, antimicrobial properties imparted to a material resulting from the present invention and its use are "sustained" when such material has long-lasting, non-leaching, antimicrobial properties not only on the surface, but also throughout the material, substrate, formed plastic product, device or other product made containing the antimicrobial agent of the present invention, if and when it is worked, molded, machined, abraded or otherwise formed into any desired product. As a result, whatever portion of the product made according to the present invention becomes the surface of such product after working, molding, machining, abrading or other forming or manufacturing process, the surface with which humans and animals have contact will be an antimicrobial surface. Such materials containing the antimicrobial polymer made using the present invention are not toxic to humans or animals.

There has been a long-felt need to provide durable, reliable, long-lasting, non-leaching antimicrobial substrates that exhibit effective antimicrobial characteristics throughout the substrate. Unfortunately, to date, no such substrates have been available from the industry, according to the pertinent prior art. Moreover, the antimicrobial agents described above are typically supplied in methanol. Methanol is toxic and explosive. There has long been a desire to provide the antimicrobial in a methanol-free form. The present invention satisfies these long-felt needs.

Until now, antimicrobial polymers of polymerized silicon-containing quaternary ammonium salt monomers have not been incorporated into medical polymers, thin layer films or laminates in hospitals or on medical devices and supplies to impart antimicrobial properties to such devices and supplies. The present invention accomplishes this in such a manner that does not compromise their biocompatibility.

Among other things, the present invention relates to a method for creating a solvent-free polymeric antimicrobial agent for manufacture of medical devices and supplies that is biocompatible and antimicrobial throughout the entire composition of the device or supply.

The present invention also relates to a method for creating a solvent-free polymeric antimicrobial agent for manufacture of medical devices and supplies that is biocompatible and antimicrobial on the surface of the device or supply.

The present invention also relates to a method for creating a solvent-free polymeric antimicrobial agent for manufacture of fabrics for clothing, outerwear, underwear, carpets, draperies, furniture and other articles containing fabric.

The present invention also relates to a method for creating an antimicrobial agent for liquid solutions.

The present invention additionally relates to a method for creating an antimicrobial agent for manufacture of a filter medium such as activated carbon, fiberglass, sand, fabrics and HEPA filtering materials.

The present invention also relates to a method for creating a biocompatible and solvent-free polymeric antimicrobial material for building materials, including paint thin films; and consumer products.

The present invention further relates to an antimicrobial laminate counter top that is not dependent on leaching antimicrobial agents for surface microbial protection.

The polymer of Formula II may be linear, cyclic, branched or cross-linked into three-dimensional networks.

The present invention additionally provides a method for creating a polymeric thin layer film or laminate having antimicrobial properties that can be applied to various medical and food supply surfaces.

BRIEF SUMMARY OF THE INVENTION

One aspect of the present invention relates to an antimicrobial polymer containing silicon-containing quaternary ammonium groups, the polymer comprising in its structure repeating units of Formula II:

$$R_3N^+R^0{}_nSiX'_{4-n}Y^-  \qquad (II)$$

wherein each R and each $R^0$ is independently a non-hydrolysable organic group; each X' is —OR', —OH or —O—Si, wherein R' is an alkyl group of 1 to about 22 carbon atoms, or an aryl group of 6 carbon atoms; n is an integer of 0 to 3; and Y is an anionic moiety suitable to form the salt of the repeating units of Formula II.

Other aspects of the present invention also relate to methods of making and using such an antimicrobial polymer.

In addition, embodiments of the present invention include a method to produce a novel composition of a solvent-free polymeric form of silicon-containing quaternary ammonium antimicrobial agents. The resulting solid polymers provide enormous benefit in allowing the antimicrobial to be blended with as example; bulk resins, coatings, and laminates during their processing. The antimicrobial agent is incorporated throughout the treated material giving a non-leaching permanence, namely, sustained antimicrobial properties.

An unexpected result was that the polymer form gives increased antimicrobial performance based on weight loadings versus the monomeric form of the silicon-containing quaternary ammonium salt. The benefits of lowering the amount of antimicrobial agent added to a product are not only economical, but also lessen the possibility of detracting from the host materials physical or chemical properties.

The prior art teaches avoiding polymer formation from the monomeric silicon-containing quaternary ammonium salts because the polymer was no longer in a viable form to treat articles. Past experience with the monomer showed that upon exposure to water the molecular weight increase due to polymer formation resulted in an intractable form that could not be used.

This invention eliminates these problems and provides an antimicrobial with many advantages in terms of incorporation into treated products, increased antimicrobial performance and reducing cost.

DETAILED DESCRIPTION OF THE PREFERRED EMBODIMENTS

Definition of Terms

In addition to terms defined herein elsewhere, the following terms have the following definitions herein:

The article "a" or "an" includes not only the singular, but also the plural of the object to which the article relates.

"Bulk resin" means a resin in any form, such as pellets, beads, flakes or powder or the like, prior to forming into a product. Often additives are blended with the bulk resin prior to forming to impart such properties as: antimicrobial, antioxidation, UV resistance, color, fire retardance, etc.

"Formed plastic product" means a polymeric resin that has been formed into a shape using various molding, extrusion, pultrusion or other forming techniques.

"Polymer" means a large molecule built up by the repetition of small chemical units (monomers). The resulting chains can be linear, cyclic, branched or cross-linked into three-dimensional networks.

"Resin" means a synthetic polymeric plastic that may be thermoplastic or thermosetting.

"Substrate" means a product to which the antimicrobial silicon-containing quaternary ammonium salt is applied or with which it is mixed or otherwise blended or reacted to impart the substrate with sustained antimicrobial properties.

"Thermoplastic" polymer or resin means a polymer where no chemical bonds form with other chains. The polymer will melt with the addition of heat.

"Thermoset" polymer or resin means a polymer where chemical bonds form between chains resulting in a 3-dimensional cross-linked structure. These polymers do not melt.

As mentioned above, one aspect of the present invention relates to an antimicrobial polymer containing silicon-containing quaternary ammonium groups, the polymer comprising in its structure repeating units of Formula II:

$$R_3N^+R^0{}_nSiX'_{4-n}Y^-$$ (II)

wherein each R and each $R^0$ is independently a non-hydrolysable organic group; each X' is —OR', —OH or —O—Si, wherein R' is an alkyl group of 1 to about 22 carbon atoms, or an aryl group of 6 carbon atoms; n is an integer of 0 to 3; and Y is an anionic moiety suitable to form the salt of the repeating units of Formula II.

One method of the present invention uses the technology of polymerizing a silicon-containing quaternary ammonium salt monomer to create a polymer with two or more silicon-containing quaternary ammonium salt repeating units to form a homopolymer in solution or as a solid. The resulting polymer has superior antimicrobial properties compared to the source monomer.

Other methods also use the technology of linking the quaternary ammonium salt monomer to an existing polymer with reactive side groups to form an antimicrobial polymer with pendant silicon-containing quaternary ammonium salt groups.

The preferred silicon-containing quaternary ammonium salt monomer used to make the polymer of Formula II has a Formula I:

$$R_3N^+R^0{}_nSiX_{4-n}Y^-$$ (I)

wherein each R and each $R^0$ is independently, a non-hydrolysable organic group; each X is, independently, a hydrolysable group; n is an integer of 0 to 3; and Y is a suitable anionic moiety to form the salt of the compound Formula I. Preferably, Y is a halide. The presently most preferred silicon-containing quaternary ammonium salt is where two of the Rs are methyl and one R is octadecyl, $R^0$ is propyl, each X is a methoxy, n is 1 and Y is chloride, such that the monomeric quaternary ammonium salt is 3-(trimethoxysilyl) propyldimethyloctadecyl ammonium chloride.

Also preferably, the quaternary ammonium salt monomer is selected from the group consisting of one of Formula III or IV:

$$(R^1)_3SiR^2N^+(R^3)(R^4)(R^5)Y^-$$ (III);

$$(R^1)_3SiR^2N(R^3)(R^4)$$ (IV);

wherein each $R^1$ is, independently, halogen or $R^6O$, where $R^6$ is H, alkyl of 1 to about 22 carbon atoms, acetyl, acetoxy, acyl, propylene glycol, ethylene glycol, polyethylene glycol, polypropylene glycol; a block polymer or copolymer of ethylene and propylene glycol, an alkyl monoether of 1 to about 22 carbon atoms of propylene glycol, ethylene glycol, polyethylene glycol, polypropylene glycol; a block polymer or copolymer of ethylene and propylene glycol or the monoester of a carbonic acid of 1 to about 22 carbon atoms and propylene glycol, ethylene glycol, polyethylene glycol, polypropylene glycol; a block polymer or copolymer of ethylene and propylene glycol; octyphenol; nonylphenol; or sorbitan ether;

$R^2$ is benzyl, vinyl or alkyl of 1 to about 22 carbon atoms;

$R^3$ and $R^4$ are, independently, lower alkyl alcohol of 1 to about 6 carbon atoms, lower alkoxy of 1 to about 6 carbon atoms, alkyl of 1 to about 22 carbon atoms; or $R^3$ and $R^4$ can, together, form a morpholine or cyclic or heterocyclic, unsaturated or saturated, five to seven-member ring of the Formula V:

$$-R^3-(R^7)_k-R^4-$$ (V)

wherein k is an integer from 0 to 2, wherein $R^7$, where the ring is saturated, is $CH_2$, O, S, NH, $NH_2^+$, $NCH_2CH_2NH_2$, $NCH_2CH_2NH_3^+$, $NCH_2CH_2N(R^8)(R^9)$, $NCH_2CH_2N^+(R^8)(R^9)(R^{10})$, N(alkyl), N(aryl), N(benzyl), wherein each $R^8$, $R^9$, and $R^{10}$ is, independently, benzyl, polyether, lower alkyl alcohol of 1 to 4 carbon atoms, lower alkoxy of 1 to 4 carbon atoms, or alkyl of 1 to about 22 carbon atoms, and wherein $R^7$, where the ring is unsaturated, is CH, N, $N^+H$, $N^+(alkyl)$, $N^+(aryl)$, $N^+(benzyl)$, $NCH_2N$, $N^+HCH_2N$, $N^+(alkyl)CH_2N$, $N^+(aryl)CH_2N$, or $N^+(benzyl)$ $CH_2N$;

wherein the ring is unsubstituted or substituted with alkyl of 1 to 22 carbon atoms, ester, aldehyde, carboxylate, amide, thionamide, nitro, amine, or halide;

$R^5$ is lower alkyl alcohol of 1 to 6 carbon atoms, $CH_2C_6H_5$, polyether, alkyl, alkoxy, perfluoroalkyl, pefluoroalkylsulfonate or perfluoroalkylcarboxylate, wherein the alkyl, alkoxy, perfluoroalkyl, perfluoroalkylsulfonate or perfluoroalkylcarboxylate is of 1 to about 22 carbon atoms, or is a five to seven-member ring of Formula V as described above; and $Y^-$ is a suitable anionic moiety to form the salt of the compound of Formula III or IV, and preferably, chloride, bromide or iodide.

Preferably, the resultant silicon-containing quaternary ammonium salt polymer has repeating units of Formula II:

wherein each R and each $R^0$ is independently a non-hydrolysable organic group, such as, without limitation, an alkyl group of 1 to about 22 carbon atoms or an aryl group, for example, phenyl; n is an integer of 0 to 3; each X' is —OR', wherein R' is an alkyl group of 1 to about 22 carbon atoms, or an aryl group of 6 carbon atoms. More preferably, each of the R groups is independently methyl, ethyl, propyl, butyl, octyl, dodecyl, tetradecyl or octadecyl; each of the $R^0$ groups is independently methyl, ethyl, propyl, butyl, octyl, dodecyl, tetradecyl or octadecyl; and each X' is —OR', wherein R' is methyl, ethyl, propyl or butyl; and even more preferably, methyl or ethyl. Preferably, Y is a suitable anionic moiety to form the salt of the polymer of Formula II, such as halide, hydroxyl, acetate, $SO_4^{-2}$, $CO_3^{-2}$ and a $PO_4^{-2}$ counter ion. More preferably, Y is a halide.

The presently most preferred silicon-containing quaternary ammonium salt repeating unit is where two of the Rs are methyl and one R is octadecyl, $R^0$ is propyl, n is 1 and Y is chloride, such that the polymer is polymeric 3-(trimethoxysilyl) propyldimethyloctadecyl ammonium chloride.

One method of preparing the preferred silicon containing quaternary ammonium polymer includes adding with agitation the silicon containing monomer to an excess of solvent, such as water, along with heat and/or a catalyst such as a mineral or organic acid or base, which initiates the polymerization process. The polymer is recovered from resulting precipitation or solvent removal.

More specifically, one embodiment of the method of making the polymer having repeating units of Formula II comprises:
  (a) providing a monomeric silicon-containing quaternary ammonium salt capable of forming the polymer having the repeating units of Formula II;
  (b) hydrolysing the monomer of Formula I with water to form Si(OH) groups; and
  (c) condensing the Si(OH) groups to form the polymer of Formula II, where X' is —O—Si.

Even more specifically, an embodiment of the method further comprises a preliminary step before step (a) that comprises dissolving the monomeric silicon-containing quaternary ammonium salt in a solvent to form a solution; the hydrolysis steps (b) further comprises mixing the solution and water preferably in the presence of heat and/or a catalyst;

the condensation step (c) preferably further comprises subjecting the solution undergoing hydrolysis to heat and/or removal of water or the other solvent to drive the reaction further to completion to form the polymer; and the method further comprises a step (d) of recovering the polymer by one of precipitation and solvent removal. A preferred further step is step (e) of drying the recovered polymer, preferably by heating to evaporate the solvent, resulting in the polymer being solvent-free, where solvent-free means that the polymer may contain residual solvent up to about 10 weight percent of the polymer.

The solvent is any suitable solvent, such as, without limitation, water, an alcohol, such as ethanol, propanol, isopropanol or butanol, a ketone, such as methyl ethyl ketone, an aldehyde, such as butyl aldehyde, an aliphatic hydrocarbon, such as pentane or hexane, an aromatic hydrocarbon, such as toluene or xylene, a glycol ether, such as diethylene glycol monomethyl ether or ethylene glycol dibutyl ether, and a halogenated hydrocarbon, such as 1,1,1-trichloroethane or tetrachloroethane. Exemplary preferred solvents include, without limitation, water, alcohols such as isopropyl alcohol and t-butyl alcohol, tetrahydrofuran, chloroform, carbon tetrachloride, ethylene glycol, propylene glycol and ethyl acetate. If water is the only solvent, there is a molar excess to hydrolyse the Si—OR groups to Si—OH. If the reaction is conducted in another solvent, a stoichiometric amount of water is then added to hydrolyse the Si—OR groups.

Preferably, the catalyst is a mineral acid, an organic acid or a base. Preferably, the acid is hydrochloric acid, sulfuric acid or acetic acid. Preferably, the base is sodium hydroxide, potassium hydroxide, ammonium hydroxide, an aliphatic amine, such as dimethylamine, tetramethylenediamine or hexamethylenediamine, a cycloaliphatic amine such as morpholine or cyclohexylamine, or an aryl amine such as aniline or diphenylamine.

Another embodiment of a method of making a polymer according to the present invention is where the polymer is a copolymer of one of a monomer and a host polymer and a polymer having repeating units of Formula II:

wherein X' is OH; and wherein the monomer and host polymer comprise functional groups capable of reacting with SiOH groups to form the copolymer. Suitable functional groups of the monomer and host polymer may include, without limitation, —OH, —C(O)OH, —NH_2, —NH, —NCO or —C(O)OR^{11}, wherein $R^{11}$ may be an aliphatic, a cycloaliphatic or an aryl group. Examples of such groups, without limitation, include an aliphatic group, such as an alkyl group of 1 to about 22 carbon atoms, for instance methyl, ethyl, propyl, butyl, octyl or dodecyl; a cycloaliphatic group, such as cyclopentane or cyclohexane; or an aryl group, such as phenyl.

The antimicrobial silicon-containing quaternary ammonium salt solution includes as a solvent for the antimicrobial agent any solvent that may effectuate the conversion of the hydrolysable groups, such as the methoxy groups, on the silicon-containing quaternary ammonium salt to OH groups. Preferably, for the antimicrobial silicon-containing quaternary ammonium salt solution, the solvent is selected based on its ability to dissolve the antimicrobial silicon-containing quaternary ammonium salt. The concentration of the solution may be about 1% to about 99% by weight of the antimicrobial silicon-containing quaternary ammonium salt. Preferably, about 1% to about 75% by weight of the antimicrobial silicon-containing quaternary ammonium salt is used, and more preferably about 1% to about 50% by weight is used.

After the silicon-containing quaternary ammonium salt monomer has been combined with the solvent, the silicon-containing quaternary ammonium salt is polymerized to form the antimicrobial homopolymer. Such polymerization preferably is achieved by mixing the solution of the silicon-containing quaternary ammonium salt monomer used to form the polymeric antimicrobial agent with a catalyst, which may be a base, such as those mentioned above, an acid, such as those mentioned above, or heat, or a combination of a base or acid and heat. The base and acid may have concentrations of about 0.0N to about 1N. An effective temperature for polymerization is about 10° C. to about 300° C., preferably about 30° C. to about 100° C., and more preferably about 20° C. to about 50° C. In general, the greater the temperature, the less time it takes for the antimicrobial polymer to form.

The method of making the antimicrobial polymer described above creates a polymeric antimicrobial silicon-containing quaternary ammonium salt, which can be incorporated into resins and materials to create substrates with sustained antimicrobial properties. The solid antimicrobial polymer can be used to treat materials by different methods of incorporating the antimicrobial polymer into the materials. Such procedures may include, for example, without limitation:

A. Dry blending the antimicrobial polymer with a bulk resin (such as in powder, flake, pellets, bead form) prior to molding.
B. Dissolving the antimicrobial polymer and bulk resin in a common solvent, then removing the solvent prior to molding.
C. Using methods A or B to make a concentrate with a portion of the bulk resin prior to blending with the remainder of the bulk resin.
D. Adding the antimicrobial polymer into coating and paint formulations.
E. Dissolving the antimicrobial polymer in a solvent to enable treatment of various materials by dipping, spraying, brushing.
F. The antimicrobial polymer can be copolymerized with other polymers as a method of incorporation into such other polymers or a bulk resin containing them.

Types of applications for the antimicrobial polymer include as examples, but not limited to, a paint thin film for use with latex or other paints for painting any surface; a laminate; a medical product; a building material, such as a counter top, roofing products like shingles, floor or ceiling tile or wall covering, doorknob, toilet handle; packaging material; paper products, toys, furniture or any other product where antimicrobial properties are desired. Other products include various types of materials or substrates, such as thermoset polymeric resin, composition wood which may include synthetic polymeric components, such as oriented strand board; plywood; paper products, textiles, activated carbon, etc.

By way of example without limitation, types of resins that can be treated with the antimicrobial polymer are: polyvinyl chloride, polyurethane, urea formaldehyde, melamine formaldehyde, polyvinyl pyrrolidone, polyvinyl alcohol, polyacrylic, polystyrene acrylic, polyvinyl acrylic, or any other suitable resin. The resin may be a thermoplastic resin or a thermoset resin.

In the embodiment of the method of the invention using the solid form of the polymerized antimicrobial silicon-containing quaternary ammonium salt, either as a polymerized coating on the host polymeric resin particles, or as discrete solid particles of the polymeric silicon-containing quaternary ammonium salt, the solid form of the antimicrobial agent may be melt blended or the like with separate resin beads, etc., to form the desired antimicrobial bulk polymeric resin. Such blending, which may be mixing, extrusion, pultrusion or the like, involves the use of a well known industrial mixer or extruder, such as but not limited to a Welex® mixer or Welex® extruder, available from Welex Incorporated, Blue Bell, Pa. The solid antimicrobial agent and the resin particles are added to the mixer in the desired proportions as set forth below and mixed at an elevated temperature where the components melt but do not degrade. The temperature should be sufficient to allow the formerly solid components to flow and uniformly blend with each other. The time to accomplish uniform blending such that a uniform mixture results varies based on the temperature and equipment used, but in general, should be sufficient to provide a uniform blend of the polymeric antimicrobial agent and the polymeric resin, whereby the resulting product will have sustained antimicrobial properties. A suitable temperature is preferably about 60° C. to about 350° C., more preferably about 100° C. to about 325° C., and even more preferably, about 150° C. to about 300° C. The mixing process results in the polymeric resin beads being evenly coated with or distributed uniformly and blended with the polymeric antimicrobial agent to form the antimicrobial bulk polymeric resin. The resulting polymeric resin has sustained antimicrobial properties that will continue to be sustained when the polymeric resin is formed into a substrate of any desired configuration, such as thin sheets for example, or any formed plastic product made from the substrate or directly from the polymeric resin.

The polymerized silicon-containing quaternary ammonium salt is "anchored" to the resin and substrate through physical blending, van der Waals forces, and chemical covalent bonding, depending on the nature of the polymeric resin substrate. The presence of the active polymeric silicon-containing quaternary ammonium group with the polymeric resin substrate has been substantiated by a dye test using Bromophenol blue. The longevity or permanence of the quaternary ammonium group has been demonstrated by dye testing the treated material after repeatedly challenging the treated host substrate with multiple hot (e.g., 140° F., 60° C.) water rinses, aging treated samples with forced air or in a microwave oven, and subjecting the treated sample to repeated boiling water for 30 minutes.

The concentration of the silicon-containing quaternary ammonium salt polymer should be less than about 50% by weight of the final bulk polymeric resin matrix to minimize adversely affecting properties of the host polymeric resin. The amount of antimicrobial agent to the host resin preferably is about 0.025% to about 50%, more preferably about 0.05% to about 20%, and even more preferably, about 0.15% to about 0.5%, where the percentages are weight percentages.

The resin substrate may be formed from a resin concentrate where a resin with a high concentration of the antimicrobial silicon-containing quaternary ammonium salt polymer is blended with the resin without any of the antimicrobial silicon-containing quaternary ammonium salt polymer in concentrations such that the final blend contains the desired amount of antimicrobial silicon-containing quaternary ammonium salt polymer. Such an antimicrobial bulk resin made from the solid polymer of the antimicrobial silicon-containing quaternary ammonium salt can be formed into a substrate of any desired shape or size using well-known plastic molding and extrusion techniques.

Tubing is manufactured by adding the antimicrobial resin beads in an extrusion mixer, such as a Welex® extruder at an elevated temperature not to exceed 350° C. Molded parts can be made by adding the antimicrobial resin beads in an injection molder at temperatures not to exceed 350° C.

If a medical device is desired, a block of the antimicrobial polymer is prepared and properly machined to the desired device dimensions.

If a thin layer film or laminate is desired, it may have any desired dimensions, based on the available equipment used to make the product. Typically, but not exclusively, the thin layer has a thickness of about 0.001 inch (0.025 mm) to about 3 inches (76.2 mm), preferably about 0.01 inch (0.25 mm) to about 1 inch (25.4 mm), and more preferably about 0.063 inch (1.6 mm) to about 0.25 inch (6.35 mm). Several layers could be made at the same time and pressed together to form a thicker layer or a laminated substrate. Multiple layers of the same material or different material can be formed into a laminate.

In addition, the present invention includes the additive or preferably synergistic combination of antimicrobial agents comprising more than one polymeric silicon-containing quaternary ammonium salt with at least one other antimicrobial agent. Other antimicrobial agents may include, by way of example and not limitation, boric acid, polyhexamethylenebiguanide, hydantoin, a silver salt and a combination thereof.

The present invention will now be described in more detail with reference to the following specific, non-limiting examples, which reflect methods of preparing the antimicrobial polymer and methods adding the polymer to various materials.

Example 1

Preparation of the Homopolymer of 3-(trimethoxysilyl) propyldimethyloctadecyl ammonium chloride Two volumes of 0.01N $NH_4OH$ in water were added slowly to one volume of a 42% by weight solution of 3-(trimethoxysilyl) propyldimethyloctadecyl ammonium chloride in methanol while stirring at room temperature. After ten minutes an additional two volumes of 0.01N $NH_4OH$ were added, stirring continued for an additional ten minutes. An additional five volumes of 0.1N $NH_4OH$ were added and stirred for an additional ten minutes. The methanol and $NH_4OH$ were removed by evaporation and the resulting polymer concentrated to 5% (wt/wt) in a rotary evaporator. The solution was dried to a methanol-free dry powder. Infrared and NMR spectroscopy confirmed the resultant powder was a homopolymer of (trimethoxysilyl) propyldimethyloctadecyl ammonium chloride. The resultant homopolymer was found to exhibit a minimum inhibitory concentration (MIC) of 0.49 µg/mL using $E.\ coli$. By comparison, the monomeric 3-(trimethoxysilyl) propyldimethyloctadecyl ammonium chloride was found to exhibit a MIC of 0.98 µg/mL. These data establish that the polymer had twice the antimicrobial efficacy against $E.\ coli$ as the starting monomer.

An independent laboratory analysis by silicone NMR determined the identity of a commercial sample (HM 4100 Lot 608-138) of the homopolymer product of the present invention prepared based on a scale up of the method of Example 1. Silicone NMR has been well established as a tool to determine the degree of substitution of siloxanes. The different degrees of substitution of siloxanes absorb at different chemical shifts in the NMR spectrum. Below are the well known T structures of siloxane:

| Chemical Structure of Silicone Species | | |
|---|---|---|
| Tri-functional silane $T_0$ | [structure shown] | R = alkyl group |
| One-degree condensation siloxane $T_1$ | [structure shown] | R = alkyl group |
| Two-degree condensation siloxane $T_2$ | [structure shown] | R = alkyl group |
| Three-degree condensation siloxane $T_3$ | [structure shown] | R = alkyl group |

Based on the analysis from the independent laboratory, the independent laboratory determined the relative mole percentages of the corresponding T structures for the product of the present invention by integrating the areas under the respective peaks corresponding to the various T structures as set forth in the following Table A, indicating a predominant mole percentage of the $T_3$ structure:

TABLE A

The Normalized $^{29}Si$ Area % or Mole % of the Chemical Components by $^{29}Si$ NMR

| Sample ID | Silane ($T_0$) $R_1$—Si—$(OR)_3$ (Mole %) | $T_1$ One-degree condensation species ≡Si—O—Si (Mole %) | $T_2$ Two-degree condensation species ≡Si—$(O-Si)_2$ (Mole %) | $T_3$ Three-degree condensation species —Si—$(O-Si)_3$ (Mole %) | Total Silane + $T_1$ + $T_2$ + $T_3$ (Mole %) |
|---|---|---|---|---|---|
| HM 4100 Lot 608-138 | 0 | 3.9 | 35.6 | 60.5 | 100 |

Example 2

Preparation of the Homopolymer of 3-(trimethoxysilyl) propyldimethyloctadecyl ammonium chloride 138 pounds (62.7 Kg) of deionized water and 3.6 pounds (1.6 Kg) of ammonium hydroxide were added to a mix tank with agitation at 70° F. (21.1° C.). 69 pounds (31.4 Kg) of 3-(trimethoxysilyl)propyldimethyloctadecyl ammonium chloride was slowly added with stirring over a 10-minute period. The resultant precipitate was filtered through a fabric filter and allowed to dry at 200° F. (93.3° C.) over an eight-hour period. The resultant solid was ground to a powder to yield powered homopolymer of 3-(trimethoxysilyl) propyldimethyloctadecyl ammonium chloride. Nuclear magnetic resonance was used to confirm the polymeric structure.

Example 3

Preparation of Fused Silica with silyl propyldimethyloctadecyl ammonium chloride Pendant Groups Five g of fumed silica (silica gel) were dispersed in 100 g of distilled water. 2.0 g of homopolymer of 3-(trimethoxysilyl) propyldimethyloctadecyl ammonium chloride prepared in Example 2 was added drop-wise at room temperature for ten minutes with vigorous stirring. The resulting modified silica was dried in a vacuum oven to produce methanol-free fumed silica polymerized with the silicon-containing quaternary ammonium salt.

Example 4

Preparation of Cast Polyvinyl Chloride (PVC) Films Containing 0.2% and 0.5% by Weight of a Homopolymer 3-(trimethoxysilyl) propyldimethyloctadecyl ammonium chloride Ten grams of polyvinyl chloride resin were dissolved in 100 g of tetrahydrofuran and 0.20 g of dry homopolymer of 3-(trimethoxysilyl) propyldimethyloctadecyl ammonium chloride was added to a beaker and dissolved by stirring. Separately, 10 g of polyvinyl chloride resin were dissolved in 100 g of tetrahydrofuran and 0.50 g of dry homopolymer of 3-(trimethoxysilyl) propyldimethyloctadecyl ammonium chloride as made in example 2 was added and dissolved by stirring. The solutions were cast on glass slides and dried in a vacuum oven. The resultant cast film was a methanol-free cast film containing PVC and the silicon-containing quaternary ammonium homopolymer.

Example 5

Antimicrobial Testing of Cast PVC Films of Example 4

Antimicrobial testing of the cast PVC films of Example 4 was carried out essentially as described in the ASTM designation E 2149-01 entitled, "Standard test Method for Determining the Antimicrobial Activity of Immobilized Antimicrobial Agents under Dynamic Contact Conditions." This test is designed to evaluate the antimicrobial properties of materials, which contain active agents that are non-leaching. The method is described briefly below.

$E.\ coli$ was grown overnight in rich media in an incubator-shaker at 37° C. while shaking at 300 rpm. After 18 hours of incubation, the bacteria were removed from the incubator and the optical density at 660 nm was measured. The culture was diluted until the optical density corresponds to a bacterial concentration of between $1 \times 10^8$ and $3 \times 10^8$ Colony Forming Units (CFU) per milliliter. The bacteria were further diluted in phosphate buffer (0.3 mM $KPO_4$ at pH 7.2) such that the working concentration was $1 \times 10^6$ to $3 \times 10^6$ CFU/mL. Test specimens were added to sterile 15 mL test tubes followed by the addition of 3 mL of the bacterial solution. An aliquot was immediately removed from the flask, serially diluted, and used to inoculate Petri plates containing nutrient agar. The plates were incubated overnight and the concentration of bacteria (CFU/mL) was thus determined. This represents the Time 0 ($T_0$) control. The tube containing the sample was placed in a shaking incubator at 37° C. and 300 rpm for one hour, at which time another aliquot was taken and tested as above. This is the treated sample ($T_F$). All tests were controlled by the inclusion of a tube that contained an untreated sample and a flask with no sample but with bacteria. The controls demonstrate that the observed reduction in bacterial count is due to the applied material and not the mechanical stress or any property of the substrate material. Log kill is a standard method to establish the ability of antimicrobial agents to destroy microorganisms. A log kill of 5.0 means that 100,000 microorganisms were destroyed on contact with the treated surface. A log kill of 6.0 establishes that 1,000,000 microorganisms were destroyed on contact with the treated surface. A log kill in excess of 5.0 is typically interpreted as an exceptionally active antimicrobial agent. The 0.2% cast film of Example 4 was found to have a log kill of 6.17 and the 0.5% cast film had a log kill of >6.30.

Example 6

Preparation of Cast Polyurethane (PU) Films Containing 0.5% by Weight of the Homopolymer of 3-(trimethoxysilyl) propyldimethyloctadecyl ammonium chloride Five grams of polyurethane resin (Tecoflex 80A, Noveon Corp.) was dissolved in 100 g of tetrahydrofuran in a beaker. 0.20 g of dry homopolymer of 3-(trimethoxysilyl) propyldimethyloctadecyl ammonium chloride prepared in Example 2, was added and dissolved by stirring. The solution was cast on glass slides and dried in a vacuum oven at 95° C. The cast film was a methanol-free film of PU and the silicon-containing quaternary ammonium homopolymer. Antimicrobial testing was carried out as described in Example 5. The antimicrobial cast film was found to have a log kill of >6.98.

Example 7

Preparation of Extruded Polyacrylate Containing 0.2% by Weight of the Homopolymer of 3-(trimethoxysilyl) propyldimethyloctadecyl ammonium chloride 50 pounds (27.7 Kg) of polyacrylate resin beads were added to an open top tank. 45.4 g of homopolymer of 3-(trimethoxysilyl) propyldimethyloctadecyl ammonium chloride prepared is Example 2 was dissolved in isopropanol and subsequently added to the open top tank. The slurry was stirred for 5 minutes, producing polyacrylate resin beads evenly coated with the homopolymer of 3-(trimethoxysilyl) propyldimethyloctadecyl ammonium chloride. Homogeneity of the coating on the resin beads was demonstrated by the following bromophenol blue test. 30 mL of 0.1% aqueous bromophenol blue were added to a 50 mL beaker. Several coated resin beads were added to the bromophenol blue solution and allowed to stand for 10 minutes. The resin beads were removed and rinsed with copious amounts of distilled water. The resin beads visually exhibited an even blue color, indicating the beads were homogeneously coated with homopolymer of 3-(trimethoxysilyl) propyldimethyloctadecyl ammonium chloride. The coated polyacrylate resin beads were injection molded into a catheter connector which had sustained antimicrobial properties as a result of the use of the beads which themselves had uniformly incorporated the antimicrobial agent as set forth above. The resultant catheter connector was tested for antimicrobial activity according to the method described in Example 5. The catheter connector was found to have a log kill of 5.34.

Example 8

Preparation of Polyvinyl Alcohol (PVOH) with Silyl propyldimethyloctadecyl ammonium chloride Pendant Groups A 4% solution of PVOH (Celvol 103, Ciba-Geigy Corporation) in water was prepared by adding 4 g of PVOH to 100 g of distilled water. The solution was heated to 190° F. (87.8° C.) with continuous stirring to dissolve the PVOH. The solution was cooled to room temperature and 1.2 grams of the homopolymer of 3-(trimethoxysilyl) propyldimethyloctadecyl ammonium chloride in methanol prepared as in Example 2 were added drop-wise for ten minutes with vigorous stirring. The solution was heated to 80° F. (26.7° C.) and allowed to react for an additional ten minutes while stirring. The resulting polymer was concentrated to 5% (wt/wt) in a rotary evaporator. The solution was dried to a methanol-free dry powder. The antimicrobial activity of the resultant polymer was determined using the test method described in Example 5 and found to have a log kill of 5.54.

Example 9

Preparation of Extruded Polyacetal Containing 0.05% by Weight of the Homopolymer of 3-(trimethoxysilyl) propyldimethyloctadecyl ammonium chloride 50 pounds (27.7 Kg) of polyacetal resin beads were added to an open top tank. 11.4 g of homopolymer of 3-(trimethoxysilyl) propyldimethyloctadecyl ammonium chloride prepare as in Example 2 was dissolved in isopropanol and subsequently added to the open top tank. The slurry was stirred for 5 minutes, producing polyacetal resin beads evenly coated with the homopolymer of 3-(trimethoxysilyl) propyldimethyloctadecyl ammonium chloride. Homogeneity of the coating was established using the bromophenol blue test. The antimicrobial resin was extruded with a commercial extrusion machine to produce extruded bar stock. The bar stock was tested for antimicrobial activity according to the test described in Example 5 and found to exhibit a log kill of 6.22 against *E. coli*.

Example 10

Preparation of Antimicrobial Activated Carbon

Coconut shell activated carbon was treated with monomeric 3-(trimethoxysilyl) propyldimethyloctadecyl ammonium chloride and polymeric 3-(trimethoxysilyl) propyldimethyloctadecyl ammonium chloride as made in Example 2 to compare the relative effectiveness of the two treatment schemes. A ladder series of treated activated carbon using the monomer and the polymeric forms of the antimicrobial agent was prepared in a pilot reactor. They were treated at levels from 0.05% to 0.5% of the antimicrobial agent to activated carbon on a weight/weight basis. The treatment scheme involved dissolving the polymer and monomer in water at their respective levels. The dilute solutions of antimicrobial agents were sprayed on the 500 g of carbon surface using a fine mist. The monomer was further treated with catalytic quantities of dilute ammonium hydroxide to polymerize the monomer on the surface of the activated carbon. After the spraying process, drying the treated carbon at 300° F. (149° C.) for two hours activated the carbon. The antimicrobial activity of the carbon was determined using the standard dynamic shake flask test described in Example 5. Results are given in the following Table 1.

Determining whether the impregnation of the carbon with antimicrobial agents had any adverse effect on the adsorption properties of the carbon was accomplished by testing the carbon tetrachloride (CTC) activity of the carbon prior to impregnation and following impregnation with the monomer and polymer forms of the antimicrobial agent. The CTC activity testing was performed by a vendor in accordance with ASTM Method D3467. The results of testing on six different samples in Table 1 indicated that there was only a marginal decrease in CTC activity after impregnation.

TABLE 1

| Wt. % Monomer | Wt. % Polymer | Log Kill | (Wt.) % CTC |
|---|---|---|---|
| 0.1 | | None | 77.6 |
| 0.25 | | 6.11 | 73.4 |
| 0.5 | | | 75.4 |
| | 0.05 | 5.92 | 75.4 |
| | 0.10 | 5.75 | 77 |
| | 0.25 | 6.18 | 78 |
| Control Carbon 0% active added | | 6.05 | 79.5 |

With the exception of the 0.1% monomer treatment level, the treated carbon was found to be very active at killing *E. coli*. As observed in tests of other materials, the polymeric form of the antimicrobial agent is more active than the monomeric form. For activated carbon, as little as 0.05% by weight of the polymer is effective.

Example 11

Preparation of Antimicrobial Paper

Multipurpose printer paper was pad coated with a 0.05% water solution of homopolymer of 3-(trimethoxysilyl) propyldimethyloctadecyl ammonium chloride made according to Example 2. The paper was allowed to air dry. Subsequent antimicrobial testing as described in Example 5 confirmed that the paper exhibits antimicrobial properties with a log kill in excess of 4.0.

Example 12

Preparation of Antimicrobial Fabric

Unbleached cotton fabric was treated with various concentration levels of both monomeric 3-(trimethoxysilyl) propyldimethyloctadecyl ammonium chloride and the homopolymer of 3-(trimethoxysilyl) propyldimethyloctadecyl ammonium chloride as prepared in Example 2. Table 2 gives the levels of treatment and the results of antimicrobial testing. In all cases 2 inch (5.1 cm) by 2 inch (5.1 cm) swatches of fabric were treated by immersing them in an aqueous solution containing the respective concentration of monomeric or polymeric 3-(trimethoxysilyl) propyldimethyloctadecyl ammonium chloride for a minimum of ten minutes. The swatches were subsequently removed from the aqueous solution and air-dried overnight. The swatches were analyzed for antimicrobial activity using ASTM E2149-01 as described in Example 5 followed by an accelerated laundering test according to AATCC 61-1996, which simulates multiple laundering effects. The swatches were again analyzed for antimicrobial activity according to ASTM E2149-01 to determine the effect of laundering on the antimicrobial activity. Results before and after laundering are given in the following Table 2. Antimicrobial activity is reported as percent reduction in $E.\ coli$ concentration. Those materials containing in excess of 0.075% monomeric 3-(trimethoxysilyl) propyldimethyloctadecyl ammonium chloride and homopolymer of -3-(trimethoxysilyl) propyldimethyloctadecyl ammonium chloride exhibit similar percent reductions for both the laundered and initial samples. At lower levels including 0.025% active agent, the homopolymeric 3-(trimethoxysilyl) propyldimethyloctadecyl ammonium chloride-treated cotton was found to exhibit superior performance when compared to the monomeric 3-(trimethoxysilyl) propyldimethyloctadecyl ammonium chloride.

TABLE 2

| % Active in Solution | Monomer Unlaundered % Reduction | Monomer-laundered % reduction | Polymer Unlaundered % reduction | Polymer Laundered % Reduction |
| --- | --- | --- | --- | --- |
| 0.010 | 22 | 0 | 27 | 0 |
| 0.025 | 38 | 0 | 99.7 | 99.28 |
| 0.050 | 95 | 98.86 | 99.7 | 99.28 |
| 0.075 | 99.59 | 99.19 | 99.99 | 99.91 |
| 0.100 | 99.99 | 99.91 | 99.99 | 99.91 |
| 0.25 | 99.99 | 99.99 | 99.99 | 99.99 |
| Control | 0 | 0 | 0 | 0 |

Example 13

Preparation of Antimicrobial Laminate

An antimicrobial laminate was prepared by dissolving 5 g of homopolymer 3-(trimethoxysilyl) propyldimethyloctadecyl ammonium chloride as prepared in Example 2 in 1000 mL of water. The mixture was allowed to sit for 1 hour. 450 g of melamine formaldehyde resin was subsequently added to the aqueous solution of homopolymer 3-(trimethoxysilyl) propyldimethyloctadecyl ammonium chloride and allowed to mix with magnetic stirring for one hour. Laminate substrate paper was immersed in the melamine formaldehyde mixture and completely saturated with the solution. The saturated laminate paper was dried in an oven at 90° C. (194° F.). The laminate paper was tested using the bromophenol blue test described in Example 7. It was determined that the antimicrobial agent was homogeneously distributed throughout the saturated laminate paper.

Example 14

Preparation of an Antimicrobial Paint Coating on Aluminum

An antimicrobial paint formulation was prepared by adding a 0.5% concentration of homopolymer 3-(trimethoxysilyl) propyldimethyloctadecyl ammonium chloride prepared as in Example 2 to a solvent-borne two-component epoxy/polyamide commercial paint coating. Aluminum slides were spray painted with the antimicrobial paint and allowed to air dry. The painted aluminum slide was tested according to the method described in Example 5 and found to exhibit a log kill of 5.52 against $E.\ coli$.

Example 15

Preparation of Antimicrobial Cotton Using a Combination of a Homopolymer of 3-(trimethoxysilyl) propyldimethyloctadecyl ammonium chloride and boric acid One g of a homopolymer 3-(trimethoxysilyl) propyldimethyloctadecyl ammonium chloride as made in Example 2 and 1 g of boric acid were added to one liter of distilled water with stirring. The mixture was allowed to age at room temperature for one hour. Ten 2 inch (5.1 cm) by 2 inch (5.1 cm) squares of natural unbleached cotton were immersed in the solution. The cotton swatches were removed and allowed to air dry for eight hours. One swatch was tested for antimicrobial activity according to the method described in example 5 and found to exhibit a log kill greater than 5.5 when subjected to $E.\ coli$.

Example 16

Preparation of Antimicrobial Cotton Using a Combination of a Homopolymer 3-(trimethoxysilyl) propyldimethyloctadecyl ammonium chloride and hydantoin 0.5 g of a homopolymer 3-(trimethoxysilyl) propyldimethyloctadecyl ammonium chloride as prepared in Example 2 and 0.5 g of hydantoin were added to one liter of distilled water with stirring. The mixture was allowed to age at room temperature for one hour. Ten 2 inch (5.1 cm) by 2 inch (5.1 cm) squares of natural unbleached cotton were immersed in the solution. The cotton swatches were removed and allowed to air dry for eight hours. One swatch was tested for antimicrobial activity according to the method described in example 5 and found to exhibit a log kill greater than 6.9 when subjected to $E.\ coli$.

Example 17

Preparation of Antimicrobial Soap

An antimicrobial liquid soap is prepared by adding 2.0 g of a homopolymer of 3-(trimethoxysilyl) propyldimethyloctadecyl ammonium chloride as prepared in Example 2 to 100 mL of a commercial liquid soap formulation. Surfaces washed with the above soap including counter tops and human hands are expected to have non-detectable microbial contamination.

Example 18

Preparation of a Antimicrobial Disinfectant

An antimicrobial disinfectant is made by dissolving 2.0 g of homopolymer 3-(trimethoxysilyl) propyldimethyloctadecyl ammonium chloride as made in Example 2 in one liter of isopropanol. A countertop surface contaminated with *E. coli* is expected to be void of *E. coli* after it is sprayed with the above solution.

Example 19

Preparation of the Homopolymer of 3-(trimethoxy) propyltrimethyl ammonium chloride 138 pounds (62.7 Kg) of deionized water and 3.6 pounds (1.6 Kg) of ammonium hydroxide are added to a mix tank with agitation at 70° F. (21.1° C.). 69 pounds of 3-(trimethoxysilyl) propyltrimethyl ammonium chloride are slowly added with stirring over a 10-minute period. The resultant precipitate is filtered through a fabric filter and allowed to dry at 200° F. (93.3° C.) over an eight-hour period. The resultant solid is ground to a powder to yield the homopolymer of 3-(trimethoxysilyl) propyltrimethyl ammonium chloride. Nuclear magnetic resonance is used to confirm the polymeric structure.

Example 20

Preparation of Antimicrobial Fabric

Unbleached cotton fabric is treated with various concentration levels of both monomeric 3-(trimethoxysilyl) propyltrimethyl ammonium chloride and the homopolymer of 3-(trimethoxysilyl) propyltrimethyl ammonium chloride as prepared in Example 19. In all cases 2 inch (5.1 cm) by 2 inch (5.1 cm) swatches of fabric are treated by immersing them in an aqueous solution containing the respective concentration of monomeric or polymeric 3-(trimethoxysilyl) propyltrimethyl ammonium chloride for a minimum of ten minutes. The swatches are subsequently removed from the aqueous solution and air-dried overnight. The swatches are analyzed for antimicrobial activity using ASTM E2149-01 as described in Example 5, followed by an accelerated laundering test according to AATCC 61-1996, which simulates multiple laundering effects. The swatches are again analyzed for antimicrobial activity according to ASTM E2149-01 to determine the effect of laundering on the antimicrobial activity. It is expected that the results before and after laundering will show that those materials containing in an appropriate minimum level of monomeric 3-(trimethoxysilyl) propyltrimethyl ammonium chloride and homopolymer of 3-(trimethoxysilyl) propyltrimethyl ammonium chloride, the homopolymeric 3-(trimethoxysilyl) propyltrimethyl ammonium chloride treated cotton will exhibit superior performance when compared to the monomeric 3-(trimethoxysilyl) propyltrimethyl ammonium chloride.

Example 21

Preparation of Antimicrobial Fabric

Unbleached cotton fabric is treated with various concentration levels of both monomeric 3-(trimethoxysilyl) propyldimethyltetradecyl ammonium chloride and the homopolymer of 3-(trimethoxysilyl) propyldimethyltetradecyl ammonium chloride that is prepared in a similar manner to the preparation of polymeric 3-(trimethoxysilyl) propyltrimethyl ammonium chloride as in Example 19. In all cases 2 inch (5.1 cm) by 2 inch (5.1 cm) swatches of fabric are treated by immersing them in an aqueous solution containing the respective concentration of monomeric or polymeric 3-(trimethoxysilyl) propyldimethyltetradecyl ammonium chloride for a minimum of ten minutes. The swatches are subsequently removed from the aqueous solution and air-dried overnight. The swatches are analyzed for antimicrobial activity using ASTM E2149-01 as described in Example 5, followed by an accelerated laundering test according to AATCC 61-1996, which simulates multiple laundering effects. The swatches are again analyzed for antimicrobial activity according to ASTM E2149-01 to determine the effect of laundering on the antimicrobial activity. It is expected that the results before and after laundering will show that those materials containing in an appropriate minimum level of monomeric 3-(trimethoxysilyl) propyldimethyltetradecyl ammonium chloride and homopolymer of 3-(trimethoxysilyl) propyldimethyltetradecyl ammonium chloride, the homopolymeric 3-(trimethoxysilyl) propyldimethyltetradecyl ammonium chloride treated cotton will exhibit superior performance when compared to the monomeric 3-(trimethoxysilyl) propyldimethyltetradecyl ammonium chloride.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as disclosed herein or as defined by the appended claims.

We claim:

1. An antimicrobial polymer in the form of a solvent-free solid homopolymer containing silicon-containing quaternary ammonium groups, the homopolymer comprising in its structure repeating units of Formula II:

$$R_3N^+R^0SiX'_3Y^- \tag{II}$$

wherein each R and $R^0$ is independently a non-hydrolysable organic group; each X' is —OR' or —OH or has been converted along with another X' on another of the repeating units to form an —O— linkage between Si atoms of respective repeating units, wherein R' is an alkyl group of 1 to about 22 carbon atoms, or an aryl group of 6 carbon atoms; and Y is an anionic moiety suitable to form the salt of the repeating units of Formula II, wherein the solvent-free solid homopolymer is in the form of discrete solid particles, wherein the solvent-free solid homopolymer is soluble and sufficiently stable to provide sustained antimicrobial properties to a substrate or formulation comprising the homopolymer dissolved in a solution, and wherein the homopolymer includes a predominant mole percentage corresponding to a $T_3$ structure.

2. The polymer according to claim 1, in which $Y^-$ is selected from the group consisting of halide, hydroxyl, acetate, $SO_4^{-2}$, $CO_3^{-2}$ and a $PO_4^{-2}$ counter ion.

3. The polymer of claim 2, wherein $Y^-$ is a halide.

4. The polymer of claim 3, wherein $Y^-$ is chloride, bromide or iodide.

5. The polymer of claim 1, wherein each R and $R^0$ is independently an alkyl group of 1 to about 22 carbon atoms, or an aryl group of 6 carbon atoms.

6. The polymer of claim 1, wherein two of the Rs are methyl and one R is octadecyl, $R^0$ is propyl, each X' is a methoxy or has been converted along with another X' on another of the repeating units to form an —O— linkage between Si atoms of respective repeating units.

7. The polymer of claim 1, wherein the polymer is polymeric 3-(trimethoxysilyl)propyldimethyloctadecyl ammonium chloride.

8. The polymer of claim 7, wherein the polymer is a homopolymer of 3-(trimethoxysilyl)propyldimethyloctadecyl ammonium chloride.

9. The polymer of claim 1, wherein the dried, solvent-free solid homopolymer is in powder form.

10. The polymer of claim 1, wherein the homopolymer is in a blend with another polymer which is different from the homopolymer.

11. The polymer of claim 1, wherein the homopolymer is soluble in an aqueous solvent.

12. The polymer of claim 1, wherein the solvent is water.

13. The polymer of claim 1, wherein the homopolymer is soluble in a non-aqueous solvent.

14. The polymer of claim 13, wherein the solvent comprises a solvent selected from the group consisting of tetrahydrofuran, isopropanol, polyvinyl alcohol and solvent-borne paint.

15. A method of making the polymer in the form of a solvent-free solid homopolymer of claim 1, the method comprising:
(a) dissolving in a solvent a monomeric silicon-containing quaternary ammonium salt capable of forming the polymer having the repeating units of Formula II;
(b) hydrolyzing the dissolved monomeric silicon-containing quaternary ammonium salt with water to form Si(OH) groups;
(c) condensing the Si(OH) groups to form the homopolymer of Formula II;
(d) recovering the homopolymer;
(e) evaporating the solvent from the recovered homopolymer, thereby resulting in the solvent-free solid homopolymer of claim 1;
(f) drying the recovered homopolymer; and
(g) grinding the dried solvent-free solid homopolymer from (f) to a form of discrete solid particles.

16. The method of claim 15, wherein the monomeric silicon-containing quaternary ammonium salt capable of forming the homopolymer having the repeating units of Formula II is a monomer of Formula I:

$$R_3N^+R^0SiX_3Y^- \quad (I)$$

wherein each R and $R^0$ is independently a non-hydrolysable organic group; each X is a hydrolysable group capable of forming X'; and Y is an anionic moiety suitable to form the salt of the repeating units of Formula II.

17. The method of claim 15, wherein the monomeric silicon-containing quaternary ammonium salt has a structure of Formula III:

$$(R^1)_3SiR^2N^+(R^3)(R^4)(R^5)Y^- \quad (III)$$

wherein $R^1$ is $R^6O$, where $R^6$ is H, alkyl of 1 to about 22 carbon atoms, acetyl, acetoxy, acyl, propylene glycol, ethylene glycol, polyethylene glycol, polypropylene glycol, octyphenol, nonylphenol, or sorbitan ether;

$R^2$ is benzyl, vinyl or alkyl of 1 to about 22 carbon atoms;

$R^3$ and $R^4$ are, independently, lower alkyl alcohol of 1 to about 6 carbon atoms, lower alkoxy of 1 to about 6 carbon atoms, alkyl of 1 to about 22 carbon atoms; or $R^3$ and $R^4$ can, together, form a morpholine or cyclic or heterocyclic, unsaturated or saturated, five to seven-member ring of the Formula IV:

$$—R^3—(R^7)_k—R^4— \quad (IV)$$

wherein k is an integer from 0 to 2, wherein $R^7$, where the ring is saturated, is $CH_2$, O, S, NH, $NH_2^+$, $NCH_2CH_2NH_2$, $NCH_2CH_2NH_3^+$, $NCH_2CH_2N$ $(R^8)(R^9)$, $NCH_2CH_2N^+(R^8)(R^9)(R^{10})$, N(alkyl), N(aryl), N(benzyl), wherein each $R^8$, $R^9$, and $R^{10}$ is, independently, benzyl, polyether, lower alkyl alcohol of 1 to 4 carbon atoms, lower alkoxy of 1 to 4 carbon atoms, or alkyl of 1 to about 22 carbon atoms, and wherein $R^7$, where the ring is unsaturated, is CH, N, $N^+H$, $N^+$(alkyl), $N^+$(aryl), $N^+$(benzyl), $NCH_2$, $N^+HCH_2N$, $N^+$(alkyl)$CH_2N$, $N^+$(aryl)$CH_2N$, or $N^+$(benzyl)$CH_2N$;

wherein the ring is unsubstituted or substituted with alkyl of 1 to 22 carbon atoms, ester, aldehyde, carboxylate, amide, thionamide, nitro, amine, or halide;

$R^5$ is lower alkyl alcohol of 1 to 6 carbon atoms, $CH_2C_6H_5$, polyether, alkyl, alkoxy, perfluoroalkyl, pefluoroalkylsulfonate or perfluoroalkylcarboxylate, wherein the alkyl, alkoxy, perfluoroalkyl, perfluoroalkylsulfonate or perfluoroalkylcarboxylate is of 1 to about 22 carbon atoms, or is a five to seven-member ring of Formula IV; and $Y^-$ is a suitable anionic moiety to form the salt of the compound of Formula III.

18. The method of claim 15, wherein the hydrolysis (b) and condensation (c) further comprise mixing the solution and water in the presence of a catalyst to form the homopolymer; and wherein the homopolymer recovery (d) comprises recovering the homopolymer by one of precipitation and solvent removal.

19. The method of claim 15, wherein the solvent is selected from the group consisting of water, an alcohol, a ketone, an aldehyde, an aliphatic hydrocarbon, an aromatic hydrocarbon, a glycol ether and a halogenated hydrocarbon.

20. The method of claim 18, wherein the catalyst is selected from the group consisting of a mineral acid, an organic acid and a base.

21. The method of claim 20, wherein the acid is selected from the group consisting of hydrochloric acid, sulfuric acid and acetic acid.

22. The method of claim 20, wherein the base is selected from the group consisting of sodium hydroxide, potassium hydroxide, ammonium hydroxide, an aliphatic amine, a cycloaliphatic amine and an aryl amine.

23. The method of claim 15, wherein the monomeric silicon-containing quaternary ammonium salt is 3-(trimethoxysilyl) propyldimethyloctadecyl ammonium chloride.

24. The method of claim 15, wherein the monomer and polymer comprise functional groups selected from the group consisting of —OH, —C(O)OH, —$NH_2$, —NH, —NCO and —C(O)$OR^{11}$, wherein $R^{11}$ is selected from the group consisting of an aliphatic group, a cycloaliphatic group and an aryl group.

25. A method of making a substrate with sustained antimicrobial properties, the method comprising:
(a) providing the substrate;
(b) providing the homopolymer of claim 1;
(c) forming a substrate with sustained antimicrobial properties by one of (i) dry blending the substrate and the homopolymer, (ii) forming a solution of the homopolymer and mixing the solution with the substrate, and (iii) coating the substrate with homopolymer.

26. The method of claim 25, wherein the substrate with sustained antimicrobial properties is made by dry blending the homopolymer with a bulk resin, then forming the substrate from the blended homopolymer and the bulk resin.

27. The method of claim 25, wherein the substrate with sustained antimicrobial properties is made by dissolving the homopolymer in a solvent to form a solution, mixing the solution with material to be used to form the substrate to form a mixture of the material and the solution, removing the solvent from the mixture to form a precursor to the substrate, and forming the precursor into the substrate with sustained antimicrobial properties.

28. The method of claim 25, wherein the substrate with sustained antimicrobial properties is made by dissolving the homopolymer in a solvent to form a solution, coating the substrate with the solution, and removing the solvent from the coated substrate to make the substrate with sustained antimicrobial properties.

29. The method of claim 26, wherein the bulk resin is a thermoplastic resin.

30. The method of claim 26, wherein the homopolymer is mixed with a thermoplastic resin to form a mixture, and the mixture is melt extruded to form the substrate with sustained antimicrobial properties.

31. The method of claim 26, wherein the homopolymer is mixed with a thermoplastic resin to form a mixture, and the mixture is injection molded to form the substrate with sustained antimicrobial properties.

32. The method of claim 26, wherein the bulk resin is a thermoset resin.

33. The method of claim 26, wherein the homopolymer is mixed with a thermoset resin to form a mixture, and the mixture is thermally processed to form the substrate with sustained antimicrobial properties.

34. The method of claim 28, wherein the substrate is metal.

35. The method of claim 28, wherein the substrate is wood.

36. The method of claim 28, wherein the homopolymer is combined with another polymer in a solvent to form an antimicrobial solution; the antimicrobial solution is coated onto the substrate, and the solvent is removed by solvent evaporation.

37. The method of claim 36, wherein the antimicrobial solution is coated onto the substrate by spraying.

38. The method of claim 28, wherein the substrate is a building material.

39. The method of claim 38, wherein the building material is selected from the group consisting of composition wood, plywood, shingles, ceiling tiles, flooring tiles, wall tiles and wall covering material.

40. The method of claim 22, wherein the base is ammonium hydroxide.

41. The method of claim 40, wherein the ammonium hydroxide is present in a concentration of about 0.3 g/L.

42. An antimicrobial polymer in the form of a solvent-free solid homopolymer containing silicon-containing quaternary ammonium groups, the homopolymer comprising a structure resulting from polymerization of units of Formula II:

$$R_3N^+R^0SiX'_3Y^-  \quad (II)$$

wherein each R and $R^0$ is independently a non-hydrolysable organic group; each X' is —OR' or —OH, wherein R' is an alkyl group of 1 to about 22 carbon atoms, or an aryl group of 6 carbon atoms; and Y is an anionic moiety suitable to form the salt of Formula II, wherein the solvent-free solid homopolymer is in the form of discrete solid particles, and wherein the solvent-free solid homopolymer is soluble and sufficiently stable to provide sustained antimicrobial properties to a substrate or formulation comprising the homopolymer dissolved in a solution, and wherein the homopolymer includes a predominant mole percentage corresponding to a $T_3$ structure.

43. The polymer of claim 42, wherein the polymerization comprises hydrolysis of the units to provide hydrolyzed units followed by condensation of the hydrolyzed units.

44. The polymer of claim 42, wherein the polymer is a homopolymer of 3-(trimethoxysilyl)propyldimethyloctadecyl ammonium chloride.

45. The solvent-free solid homopolymer of claim 42, wherein the homopolymer is in powder form.

46. A solvent-free solid homopolymer made by a process comprising:
(a) dissolving in a solvent a monomeric silicon-containing quaternary ammonium salt to obtain a solution, the monomeric silicon-containing quaternary ammonium salt having the following Formula I:

$$R_3N^+R^0SiX_3Y^-  \quad (I)$$

wherein each R and $R^0$ is independently a non-hydrolysable organic group; each X is, independently, a hydrolysable group, and Y is a suitable salt-forming anionic moiety;
(b) hydrolyzing the dissolved monomeric silicon-containing quaternary ammonium salt with water to form Si(OH) groups;
(c) condensing the Si(OH) groups to form a condensed polymer;
(d) recovering the condensed polymer to obtain a recovered polymer;
(e) evaporating the solvent from the recovered polymer, thereby resulting in the solvent-free solid homopolymer;
(f) drying the recovered homopolymer; and
(g) grinding the dried solvent-free solid homopolymer from (f) to a form of discrete solid particles,
wherein the solvent-free solid homopolymer is soluble and sufficiently stable to provide antimicrobial properties to a substrate or formulation comprising the homopolymer dissolved in a solution, and wherein the homopolymer includes a predominant mole percentage corresponding to a $T_3$ structure.

47. The solvent-free solid homopolymer of claim 46, wherein the hydrolysis (b) and condensation (c) comprise mixing the solution and water in a presence of a catalyst to form the condensed polymer; and wherein the recovery (d) comprises recovering the condensed polymer by precipitation or solvent removal.

48. The solvent-free solid homopolymer of claim 46, wherein the solvent is selected from the group consisting of water, an alcohol, a ketone, an aldehyde, an aliphatic hydrocarbon, an aromatic hydrocarbon, a glycol ether and a halogenated hydrocarbon.

49. The solvent-free solid homopolymer of claim 46, wherein the hydrolysis (b) and condensation (c) are carried out in a presence of a mineral acid, an organic acid or a base as a catalyst.

50. The solvent-free solid homopolymer of claim 49, wherein the acid is hydrochloric acid, sulfuric acid or acetic acid.

51. The solvent-free solid homopolymer of claim 49, wherein the base is sodium hydroxide, potassium hydroxide, ammonium hydroxide, an aliphatic amine, a cycloaliphatic amine or an aryl amine.

52. The solvent-free solid homopolymer of claim 51, wherein the base is ammonium hydroxide.

53. The solvent-free solid homopolymer of claim 52, wherein the ammonium hydroxide is present in a concentration of about 0.3 g/L.

54. The solvent-free solid homopolymer of claim 46, wherein the monomeric silicon-containing quaternary ammonium salt is 3-(trimethoxysilyl)propyldimethyloctadecyl ammonium chloride.

55. The solvent-free solid homopolymer of claim 46, wherein the polymer is in powder form.

56. The solvent-free solid polymer of claim 46, wherein the homopolymer is in a blend with another polymer which is different from the solvent-free solid homopolymer.

* * * * *